United States Patent [19]

Häkkinen

[11] Patent Number: 5,063,922

[45] Date of Patent: Nov. 12, 1991

[54] ULTRASONIC ATOMIZER

[75] Inventor: Taisto Häkkinen, Hämeenlinna, Finland

[73] Assignee: Etala-Hameen Keuhkovammayhdistys R.Y., Finland

[21] Appl. No.: 382,657

[22] PCT Filed: Oct. 27, 1988

[86] PCT No.: PCT/FI88/00176

§ 371 Date: Aug. 7, 1989

§ 102(e) Date: Aug. 7, 1989

[87] PCT Pub. No.: WO89/06147

PCT Pub. Date: Jul. 13, 1989

[30] Foreign Application Priority Data

Dec. 31, 1987 [FI] Finland .................... 875797

[51] Int. Cl.$^5$ .................... A61M 11/00; A61M 15/00
[52] U.S. Cl. .................... 128/200.16; 128/200.14; 128/203.12
[58] Field of Search .................... 128/200.16, 200.14, 128/203.12, 204.26, 204.21

[56] References Cited

U.S. PATENT DOCUMENTS

| | | | |
|---|---|---|---|
| 3,490,697 | 1/1970 | Best, Jr. .................... | 128/200.16 |
| 3,561,444 | 2/1971 | Boucher .................... | 128/194 |
| 3,812,854 | 5/1974 | Michaels et al. .................... | 128/194 |
| 3,828,773 | 8/1974 | Buch et al. .................... | 128/200.16 |
| 3,861,386 | 1/1975 | Harris et al. .................... | 128/194 |
| 3,989,042 | 11/1976 | Mitsui et al. .................... | 128/200.16 |
| 4,001,650 | 1/1977 | Romain .................... | 128/200.16 |
| 4,113,809 | 9/1978 | Abair et al. .................... | 128/200.16 |
| 4,319,155 | 3/1982 | Nakai et al. .................... | 128/200.16 |
| 4,396,015 | 8/1983 | Johnson .................... | 128/200.14 |
| 4,677,975 | 7/1987 | Edgar et al. .................... | 128/200.14 |
| 4,819,629 | 4/1989 | Jonson .................... | 128/200.16 |

FOREIGN PATENT DOCUMENTS

| | | |
|---|---|---|
| 283190 | 2/1980 | Fed. Rep. of Germany . |
| 3013964 | 10/1981 | Fed. Rep. of Germany .................... 128/200.16 |
| 2041249 | 9/1980 | United Kingdom .................... 128/200.16 |

Primary Examiner—Edgar S. Burr
Assistant Examiner—Kimberly L. Asher
Attorney, Agent, or Firm—Steinberg & Raskin

[57] ABSTRACT

The invention concerns an ultrasonic atomizer (10), which is intended for an inhalation treatment apparatus for persons suffering from respiratory diseases. The ultrasonic atomizer (10) comprises an atomizer device (11) provided with a drug container (12) as well as an ultrasonic oscillator (13) connected to the container (12), the oscillator preferably comprising an oscillating crystal. The atomizer device (11) is provided with a duct passing into the patient, advantageously a mouth piece and an air-inlet duct (15). The atomizer device (11) comprises a pressure detector (36) directly connected to it or a duct (16) that is connected to the atomizer device (11) and passes to the pressure detector (36) and transmits the pressure of the breathing air. The pressure detector (36) detects the changes in pressure resulting from inhalation or exhalation of the patient, whereby, starting from the beginning of the inhalation stage, atomizing can be switched on by the apparatus. The ultrasonic atomizer (10) comprises a regulating device (18) connected to the atomizer (11), by means of which regulator the operation of the ultrasonic oscillator (13) is regulated. The regulating device (18) and the atomizing device (11) are interconnected by means of an electrical connection (17), whereby, through this connection (17), an electrical oscillation can be supplied to the crystal present in the ultrasonic oscillator. The electric oscillation can be coverted to mechanical oscillation of the crystal. The apparatus comprises circuitry for switching on of the ultrasonic oscillator (13) at least when the inhalation stage of the patient begins. Also, a timing device (44) is provided, by which the duration of operation of the ultrasonic oscillator (13) can be regulated as desired.

1 Claim, 5 Drawing Sheets

ULTRASONIC ATOMIZER

BACKGROUND OF THE INVENTION

The invention concerns an ultrasonic atomizer, which is intended for an inhalation treatment apparatus for persons suffering from respiratory diseases, said ultrasonic atomizer comprising an atomizer device provided with a drug container as well as an ultrasonic oscillator connected to the container, preferably an oscillating crystal, and said atomizer device being provided with a duct passing into the patient, advantageously a mouth piece and an air-inlet duct, and said atomizer device comprising a pressure detector directly connected to the atomizer device or a duct that is connected to the atomizer device and passes to the pressure detector and transmits the pressure of the breathing air, whereat the pressure detector detects the changes in pressure resulting from inhalation or exhalation of the patient, whereby, starting from the beginning of the inhalation stage, atomizing can be switched on by the apparatus, and said ultrasonic atomizer comprising a regulating device connected to the atomizer device, by means of which regulating device the operation of the ultrasonic oscillator is regulated.

Water or drug mist that is used in respiration treatment can also be produced by means of ultrasonic oscillations. By means of intensive oscillation, a field of waves is produced on the surface of liquid, in which the velocity of the liquid particles in the waves becomes so high that it surpasses the effects of gravity and of surface tension forces, and small particles are detached from the liquid surface into the air. The drop size is determined by the properties of the liquid and by the ultrasonic frequency used in the ultrasonic oscillator. Most commonly, the ultrasonic frequency in treatment atomizers is of an order of 1 to 2 MHz. In such a case the drop size of water mist becomes 2 to 5 $\mu$m. The atomizing capacity of the ultrasonic atomizer depends on the size of the oscillating crystal and on the magnitude of the electric power supplied to the crystal. For example, with a crystal of a diameter of about 15 mm and with a power of about 12 W, the water atomizing capacity that is obtained is about 250 ml/h.

A drawback of the prior art ultrasonic atomizers is the short service life of the oscillator crystal. Nor has a precise adjustment of the atomizing been possible in the prior art ultrasonic atomizers. Thus, it would be an improvement if the atomizing time could be adjusted so that it is advantageous in view of the treatment of the patient. Therefore, an apparatus would be advantageous in which the optimal atomizing time can be adjusted individually for each patient. In view of the short service life of the apparatus, it would also be advantageous to be able to form an ultrasonic atomizer in which it is possible to increase the service life of the ultrasonic crystal considerably, without deterioration of the treatment results.

SUMMARY OF THE INVENTION

The objects hereinbefore stated of the invention have been achieved by means of an apparatus which is mainly characterized in that the regulating device and the atomizing device are interconnected by means of an electric connection, whereby, through said connection, an electric oscillation can be supplied to the crystal present in the ultrasonic oscillator (13), whereby said electric oscillation can be converted to mechanical oscillation of the crystal, and that means are provided for switching on said ultrasonic oscillator at least when the inhalation stage of the patient begins and that a timing device is provided by means of which the duration of operation of the ultrasonic oscillator can be regulated.

An ultrasonic atomizer in accordance with the invention includes a control between the pressure detector and the timing device, whereby the pressure detector detects any change in pressure resulting from the inhalation of the patient, and further, the signal thereat arriving from the pressure detector is adapted to start the counting of the timing device from the beginning of the inhalation stage. By means of the regulating device, the maximum time that the ultrasonic oscillator oscillates can be set in advance into the timing device. The ultrasonic atomizer in accordance with the invention also includes a control logic which detects when the liquid in the container has been exhausted, in which case the control logic detects the quantity of liquid present in the container from a change in the current or voltage of the oscillating crystal. When current or voltage values higher or lower than certain predetermined values are reached, the control logic switches the crystal off oscillation. The control logic also includes means by which it is ensured that the crystal cannot be switched on oscillation until after the main current circuit has first been switched off once. Thereby it is ensured that liquid is added to the liquid vessel.

The ultrasonic atomizer in accordance with the invention also includes an infrared detector, which detects whether the duct connected to the pressure detector and transmitting negative pressure is connected to the regulator device. When the connector of the duct is not connected to the regulator device, the infrared detector detects this, and then the apparatus atomizes constantly.

The apparatus in accordance with the invention also includes connector means by which the ultrasonic oscillator can be connected detachably to a liquid container. In this way, the same ultrasonic oscillator can be used in connection with several different atomizers or liquid containers.

BRIEF DESCRIPTION OF THE DRAWINGS

In the following, the invention will be described with reference to some preferred embodiments of the invention illustrated in the figures in the accompanying drawings, the invention, however, not to be confined to said embodiments alone.

FIG. 1A is an axonometric view of an ultrasonic atomizer in accordance with the invention.

FIG. 1B shows the device of FIG. 1A with the duct of negative pressure disconnected from the regulator device.

FIG. 1C shows the device of FIG. 1A as viewed from the rear and in the direction of the arrow K in FIG. 1A.

FIG. 2A is a side view of the atomizer with the flow ducts inside the apparatus shown with broken lines.

FIG. 2B shows the apparatus of FIG. 2A with the ultrasonic oscillator disconnected.

FIG. 3 shows an ultrasonic atomizer in accordance with the invention as an operational block diagram.

DESCRIPTION OF THE PREFERRED EMBODIMENTS

Figure 1A:
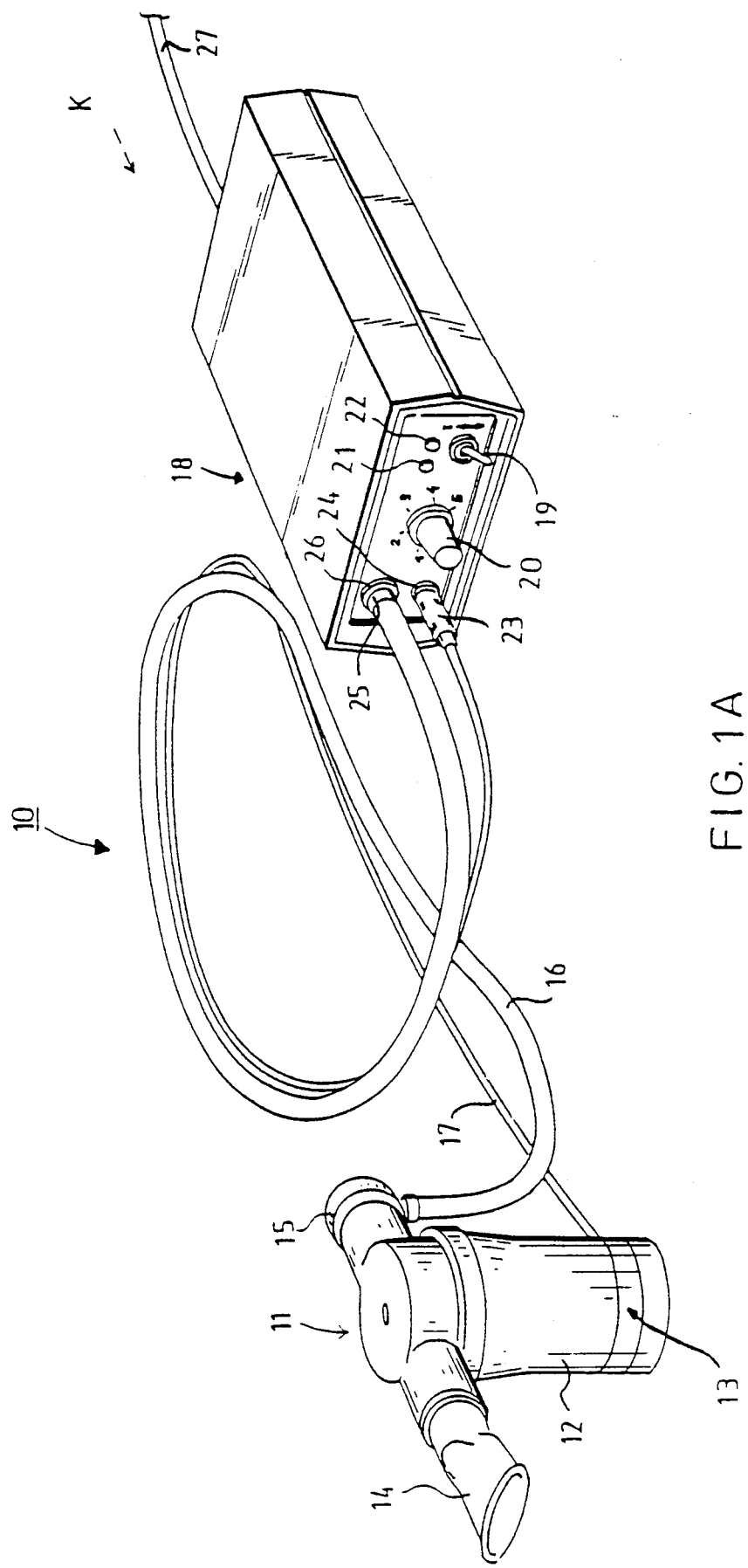
Figure 1B:
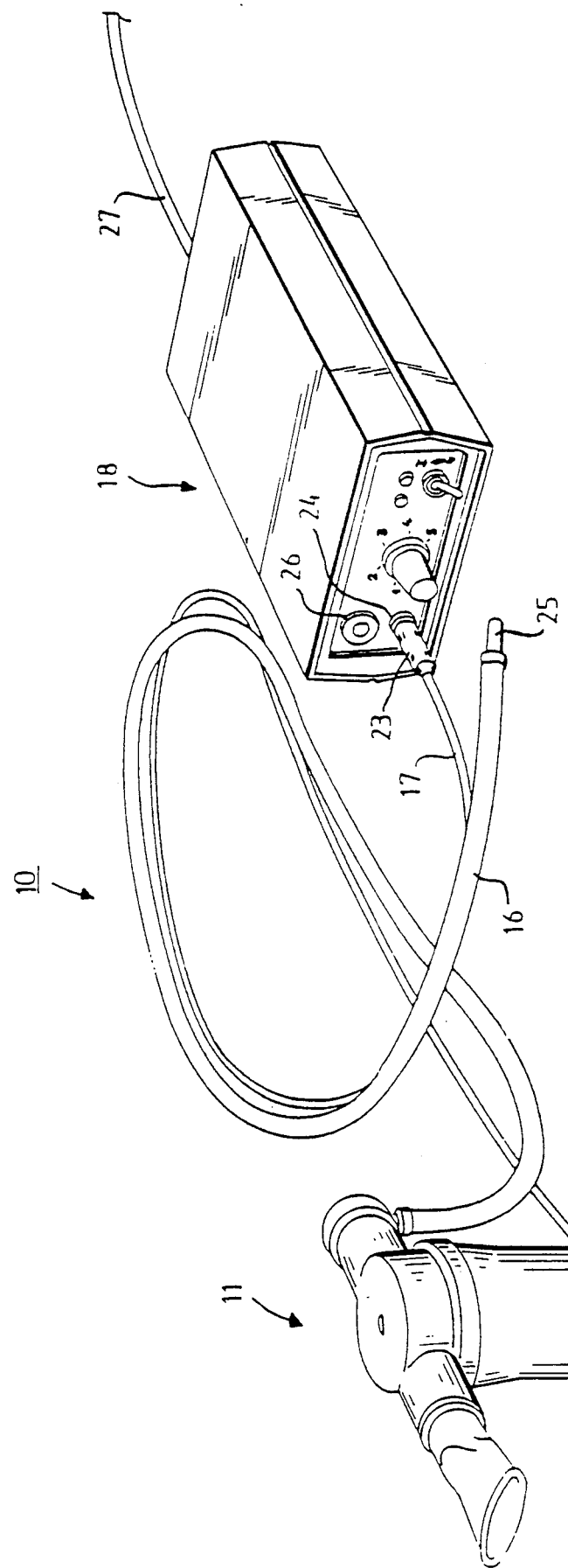
Figure 1C:
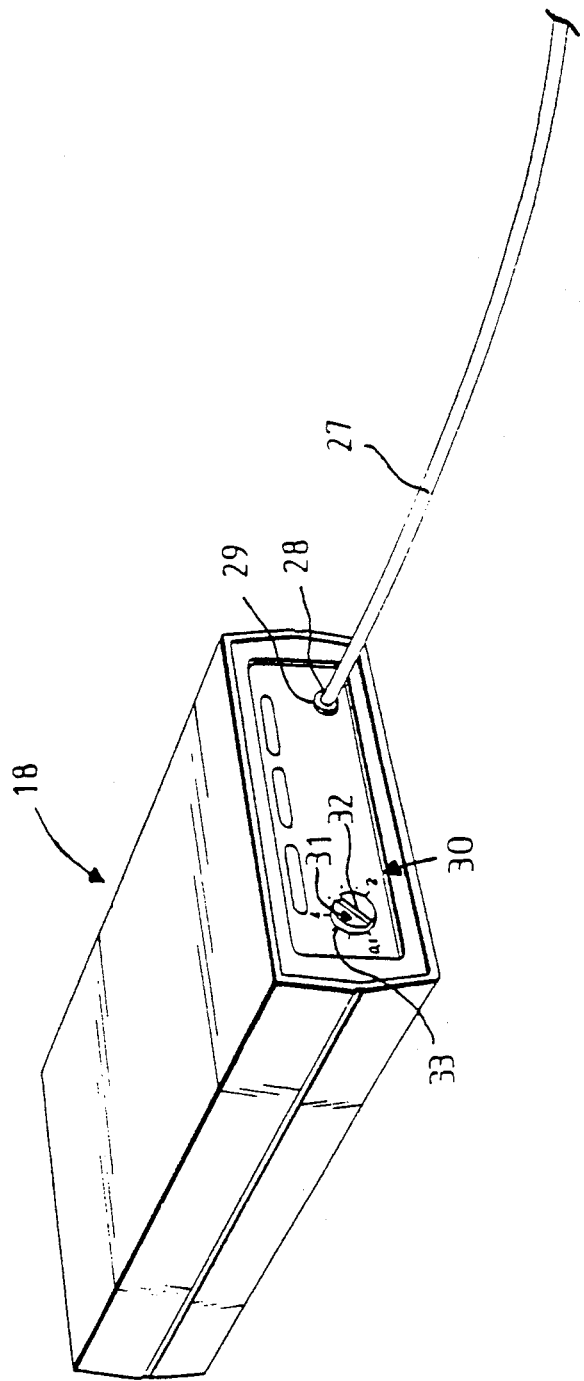
Figure 2A:
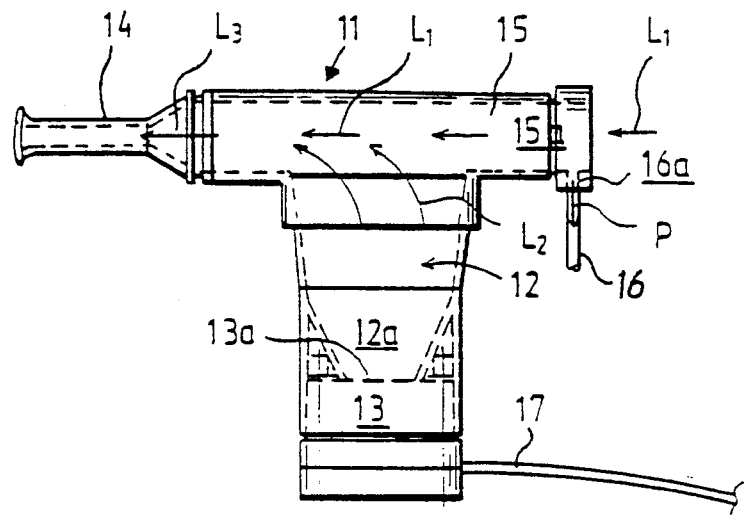
Figure 2B:
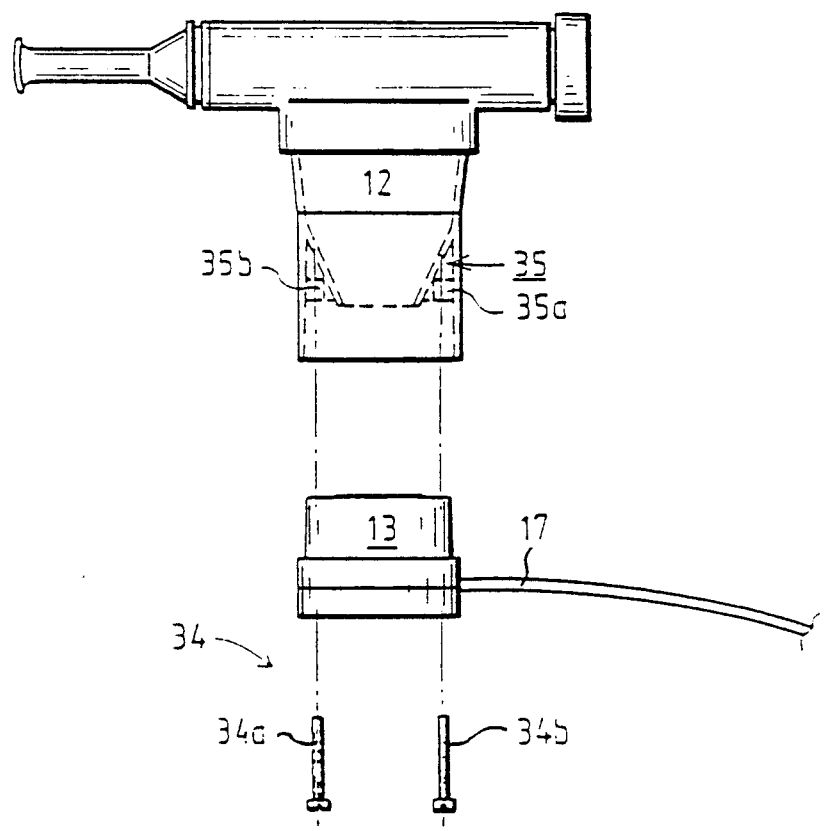

FIG. 1A is an axonometric view of an ultrasonic atomizer 10 in accordance with the invention. The ultrasonic atomizer 10 comprises an atomizer device 11 and a liquid container 12 provided therein, an ultrasonic oscillator 13 being fitted at the bottom of the container.

The ultrasonic oscillator 13 comprises an oscillating crystal, the oscillation energy being transferred from the oscillating crystal to the surface of the liquid, preferably a drug, contained in the liquid vessel, whereby a wave field is formed on the surface of the liquid. The velocity of the liquid particles in the waves becomes so high that it surpasses the effects of gravity and surface tension forces, and small particles are detached from the liquid surface into the air. The drops are carried from the liquid vessel further into the air space passing into the patient.

The atomizer device 11 further comprises a connecting duct 14 passing to the patient, as well as an air-inlet duct 15 connected to the atomizer. The connecting duct 16 connected to the pressure detector is fitted so that it is advantageously connected to the inlet duct 15. The connecting conduit passing the oscillating power to the crystal is denoted with the reference numeral 17, and said conduit is favorably an electrical conduit, preferably a coaxial cable.

The ultrasonic atomizer 10 in accordance with the invention includes a regulator device 18, which contains all essential regulating circuits and regulating functions related to the apparatus in a single housing.

The regulator device 18 includes a main current switch 19 and a power regulator 20 for the ultrasonic oscillator. Further, located on the front panel of the regulator device, there is a first signal light 21, which is the signal light of the main current circuit and, when it is on, indicates that the current is on, and when the signal light is off, the current has been switched off. At the side of the first signal light, in the front panel, there is a second signal light 22, which indicates that the liquid is being exhausted in the liquid vessel 12.

As is shown in FIG. 1B, the conduit 17 is provided with a connector 23, by means of which the conduit 17 can be connected to the mating connector 24, provided on the regulator device 18, detachably.

Correspondingly, the connecting duct 16 of the pressure detector 36 is provided with a connector 25, by means of which the duct 16 can be connected to the mating connector 26, detachably provided on the regulator device 18, detachably. The reference numeral 27 denotes the voltage cable through which the operating power is supplied into the apparatus. It is also self-evident that it is possible to connect an accumulator or any other source of power to the regulator device 18.

FIG. 1C is a rear view of the regulator device 18, seen in the direction of the arrow K in FIG. 1A. In the way shown in FIG. 1C, the voltage cable 27 includes a connector 28, which can be connected further to the mating connector 26 provided on the regulator device 18. As was already explained above, an accumulator or any other source of power can be connected to the mating connector 29 directly.

In the illustration shown in FIG. 1C the adjusting knob 30 of the atomizing-time timing device 44, placed on the rear panel of the device, is shown. The adjusting knob 30 comprises an indicator arrow 31 or equivalent and an adjusting slot 32, by means of which the adjusting knob can be turned and the atomizing time be adjusted to the desired level. The rear panel is provided with a time scale 33, from which the desired atomizing time can be read as indicated by the indicator arrow 31.

FIG. 2A is a side view of the atomizing device 11 to be connected to the regulator device 18, the air ducts inside the apparatus being shown by broken lines. When the patient breathes through the connecting duct, i.e. the mouthpiece 14, passing into the patient, air is entrained from the outer air in the direction shown by the arrow $L_1$ through the duct 15 and the drug is carried from the liquid vessel 12 along with the air flow $L_1$ in the direction shown by the arrow $L_2$ into the connecting duct 14 that passes into the patient, and further the air with the atomized substance are carried into the patient as is shown by the arrow $L_3$. As the patient inhales through the connecting duct 14, a flow is produced in the duct 15, and further a negative pressure is formed at the connection point 16*a*, to which the connection hose 16 passing to the pressure detector is connected. The negative pressure (P) is transmitted through the connection hose 16 to the pressure detector in the regulator device 18.

The bottom portion of the container part 12*a* of the liquid container 12 is constituted by the top portion 13*a* of the ultrasonic oscillator 13. Thus, said top portion 13*a*, which transmits the oscillation of the crystal, acts as the bottom portion of the liquid container 12, favorably the drug container. In this embodiment of the invention, a liquid container 12 is recited, which means a container which may contain water or a drug to be atomized or any other treatment agent to be atomized.

Along the cable 17, a variable electric voltage is passed to the crystal in the ultrasonic oscillator 13.

As is shown in FIG. 2B, the ultrasonic oscillator 13 can be detached from the liquid container 12. Thus, the same ultrasonic oscillator can be used for different atomizers 11 and for different liquid containers 12, e.g., for administration of different medicines.

As is shown in FIG. 2B, the apparatus includes connecting means 34,35, by which the ultrasonic oscillator 13 can be connected to the liquid vessel 12 detachably. As is shown in FIG. 2B, the side faces of the drug container 12 are provided with attachments 35, which, as shown in the Figure, consist of two cavities 35*a*,35*b*, into which the attaching members 34 that grasp the ultrasonic oscillator 13 are coupled detachably. As is shown in FIG. 2B the attaching members 34 consist of screws 34*a*,34*b*, which said screws attach the ultrasonic oscillator 13 to the liquid container 12 when they are engaged into the screw cavities 35*a* and 35*b*.

FIG. 3 shows a functional block diagram of the ultrasonic atomizer. According to the invention, a quartz crystal or any other corresponding oscillating crystal is made to oscillate depending on the inhalation stage of the patient. When the patient breathes through the connecting duct 14, i.e. the mouthpiece, air flow passes through the duct 15 into the open air, and the pressure is lowered in duct 15. The negative pressure (P) is transmitted through the connection 16*a* along the hose 16 to the pressure detector 36 provided in the regulator device 18.

Within the scope of the invention, an embodiment of the invention is also contemplated in which the pressure detector 36 is placed directly in the atomizing device 11, e.g., in its air-inlet duct 15. In such a case, the conduit passing from the pressure detector to the regulator device 18 may be an electrical one.

According to the invention, the apparatus further includes a timing device 44, in which the desired duration of atomizing can be preset by means of the atomizing-time regulator 30. When inhalation begins, the pressure in the duct 15 is lowered and the negative pressure concerned is detected by the pressure detector 36. The pressure detector 36 is connected to the timing device 44 electrically, and when the inhalation begins and the pressure detector 36 detects said start of inhalation, the information is transmitted to the timing device 44, which, by means of the control logic and by the intermediate of the power oscillator 51 keeps the quartz crystal oscillating for the time preset in the timing device 44 by means of the regulator 30. When the time preset by means of the atomizing-time regulator 30 is exceeded, the control logic switches off the power oscillator and the ultrasonic oscillator 13 stops oscillating. Thereby, transfer of treatment agent into the air passing into the patient is also prevented.

The source of power may be either an accumulator or a commercial power supply connection unit, which is connected to the voltage connector placed in the rear panel of the device.

The apparatus can be used in either of two ways. Thus, by means of the apparatus it is possible to perform either atomization regulated by the patient's breathing, or constant atomization.

When the atomization is controlled by the patient's breathing, the small negative pressure produced at the beginning of the inhalation stage of the patient is transferred along the hose 16 to the regulator device 18 and to the pressure detector 36 provided therein, said detector producing voltage on the basis of the pressure. This voltage is amplified in an amplifier 39, and a signal therefrom starts the timing device 44. At the same time, the control logic 46 switches on the power oscillator 51 which then oscillates at an ultrasonic frequency. This electrical oscillation is passed along a coaxial cable 17 to the crystal, preferably a quartz crystal, in the ultrasonic oscillator denoted with the reference numeral 13. The quartz crystal converts the electrical oscillation to mechanical oscillation. The mechanical oscillation is transferred into the liquid placed in space 12a in the liquid container 12, which liquid is atomized more efficiently the higher the power regulator 20 has been set.

With the voltage data received at the beginning of the exhalation stage, the timing circuit is reset to zero and the control logic switches the power oscillator off operation and the atomizing is discontinued.

If the inhalation stage lasts longer than the time preset in the timing device, the timing device switches off the atomizing at the preset time. The infrared detector 47 detects when the hose connector 25 is inserted in the corresponding connector 26 of the regulator device 18. Thereby the apparatus operates automatically while being controlled by the patient's breathing.

In the case of constant atomization, the hose connector 25 of the pressure detector is not inserted in the corresponding connector 26 of the regulator device 18. In such a case, the apparatus atomizes constantly independently of the patient's breathing. In the case of constant atomizing, the power regulation operates in a similar way as in the case of atomization controlled by the patient's breathing.

The current monitoring electronics 62 operate with both modes of operation. When the liquid is exhausted in the liquid container 12, the input current is lowered and thereby the control logic 46 switches off the atomizing. The indicator light 22 indicates to the operator that the liquid has been exhausted. The apparatus does not restart atomizing until the current switch 19 has been turned to the off position for a moment. The current indicator light 21 indicates whether the current is on or off in the apparatus.

Figure 3:
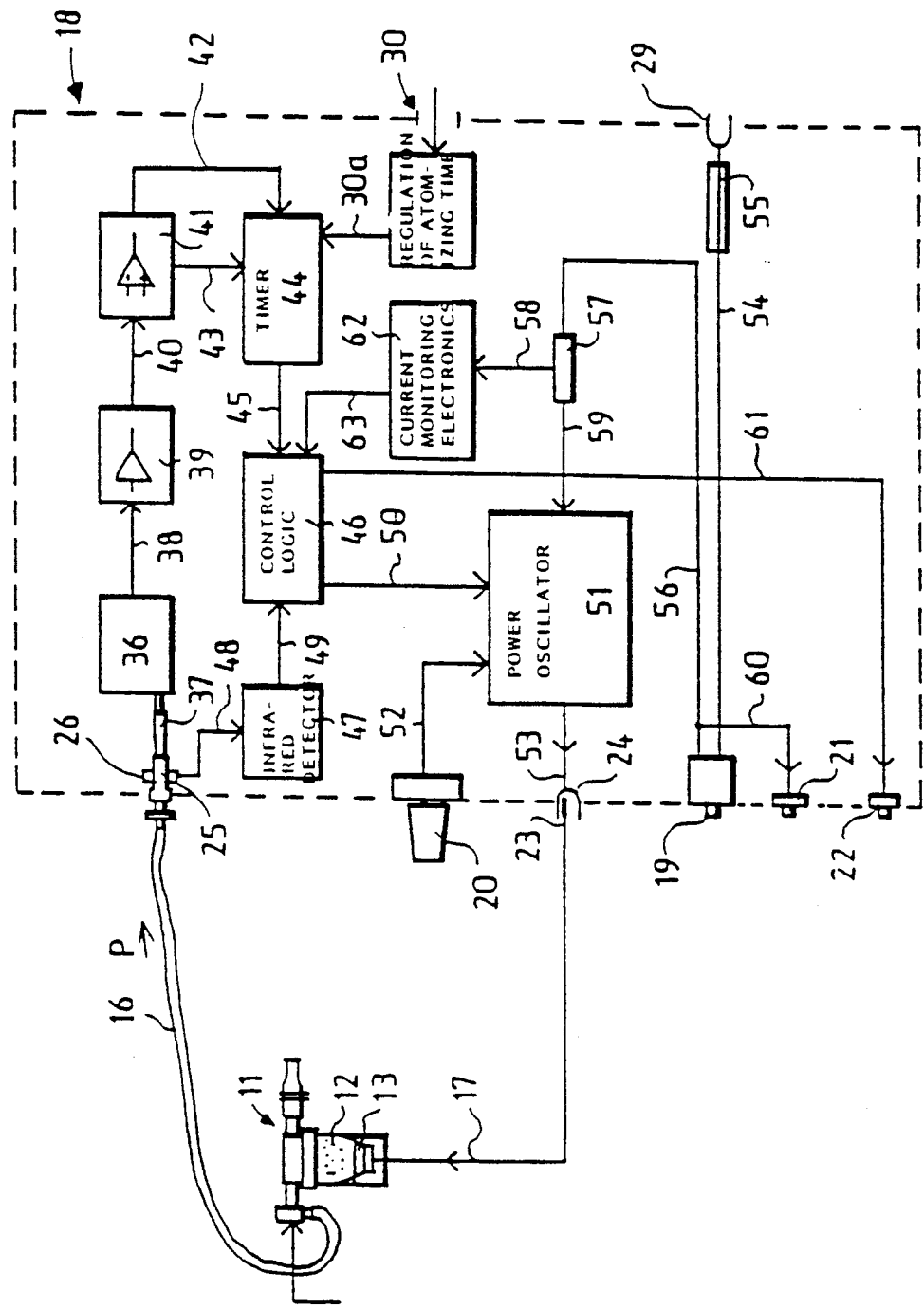

In the following, based on FIG. 3, the connections between the block diagrams will be described. Negative pressure arrives in the pressure detector 36 along the duct 37. The pressure detector transmits the voltage along the signal path 38 to the signal amplifier 39, which transmits the amplified voltage further along the signal path 40 to the trigger and reset device. From the trigger and reset device 41 there are outputs for trigging along the signal path 43 and for reset along the signal path 42. Said signal paths are connected to the timing device 44 as inputs. From the atomizing-time regulator 30, the preset atomizing time is passed along the signal path 30a to the timing device.

From the timing device there is a signal path 45 further to the control logic 46. Further inputs to the control logic are the signal path 49 from the infrared detector 47, and the infrared detector 47 receives the signal detecting the presence of the connector 25 along the signal path 48 as an input. From the current monitoring electronics 62 the control logic 46 receives an input along the signal path 63. The output 50 of the control logic is connected to the power oscillator 51, to which the power regulation is also connected along the path 52. The current from the connector 29 comes through a fuse 55 along the current conduit 54 to the current switch 19 and further, from the current switch 19 the current is passed along the current conduit 56 to the current distribution point 57, and from there further to the current monitoring electronics 62 along the current conduit 58 and to the power oscillator 51 along the current conduit 59. From the power oscillator 51 there is an output 53 through the connectors 23,24 to the coaxial cable 17 passing to the crystal.

From the control logic 46 there is a connection to the signal light 22 indicating exhaustion of the liquid along the signal path 61, and correspondingly there is a signal path 60 to the current signal light 21 from the branch 56 connected to the current switch 19.

What is claimed is:

1. An ultrasonic atomizer for an inhalation treatment apparatus for patients suffering from respiratory diseases, said ultrasonic atomizer comprising an atomizer device provided with a liquid container and an ultrasonic oscillator, said ultrasonic oscillator comprising an oscillating crystal connected to said liquid container, said atomizer device being provided with a duct for direct connection to a patient and an air-inlet duct, a detector connected to the atomizer device which detects changes in pressure resulting from inhalation and exhalation of the patient, and initiating atomizing at the beginning of an inhalation stage, a regulating device connected to the atomizer device and regulating the operation of the ultrasonic oscillator, an electrical connection means interconnecting the regulating device and the atomizing device, said electrical connection means supplying an electrical oscillation to the crystal in the ultrasonic oscillator, whereby said electrical oscillation is converted to oscillation of the crystal, and further comprising a timing device for regulating the maximum time of operation of said ultrasonic oscillator, said timing device connected to said detector and switching on said ultrasonic oscillator at least when the inhalation stage of the patient begins;

a control means connected between the detector and the timing device, whereby a signal arriving from the detector is adapted to start counting on the timing device from the beginning of the inhalation stage, said regulator device being connected to the timing device, said timing device adapted to be preset to provide a maximum time of oscillation for a particular patient during which time said liquid is atomized into the patient, said regulator turning off said oscillator when said timing device counts to said preset maximum time; and further comprising a duct connected between said atomizer device and said detector for transmitting said changes resulting from inhalation and exhalation of the patient; and a connector attached to one end of the duct, and an infrared detector, which detects whether the duct connected to the detector and transmits negative pressure has been connected to the regulator device, and if the connector attached to the duct has not been connected to the regulator device, the infrared detector detects this, and the apparatus atomizes constantly.

* * * * *